US00PP22847P3

(12) United States Plant Patent

Klemm et al.

(10) Patent No.: US PP22,847 P3

(45) Date of Patent: Jul. 10, 2012

(54) POINSETTIA PLANT NAMED 'NPCW10184'

(50) Latin Name: *Euphorbia pulcherrima Willd. ex Klotzsch*
Varietal Denomination: NPCW10184

(75) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 5 days.

(21) Appl. No.: 12/925,793

(22) Filed: Oct. 29, 2010

(65) Prior Publication Data

US 2012/0110711 P1 May 3, 2012

(51) Int. Cl.
*A01H 5/00* (2006.01)

(52) U.S. Cl. ..... Plt./306

(58) Field of Classification Search ..... Plt./306
See application file for complete search history.

(56) References Cited

U.S. PATENT DOCUMENTS

PP18,484 P3 * 2/2008 Zerr ..... Plt./303
PP19,020 P2 * 7/2008 Klemm ..... Plt./307

OTHER PUBLICATIONS

Broertjes et al. "Application of Mutation Breeding Methods in the Improvement of Vegetatively Propagated Crops," 1978, pp. 118-119.*

* cited by examiner

*Primary Examiner* — Susan McCormick Ewoldt
(74) *Attorney, Agent, or Firm* — Jondle & Associates, P.C.

(57) ABSTRACT

A new poinsettia plant named 'NPCW10184' particularly distinguished by its upright growth habit and intensive marbling color pattern is disclosed.

1 Drawing Sheet

Genus and species: *Euphorbia pulcherrima* Willd. ex Klotzsch.
Variety denomination: 'NPCW10184'.

BACKGROUND OF THE NEW PLANT

The present invention comprises a new and distinct variety of poinsettia plant, botanically known as *Euphorbia pulcherrima* Willd. ex Klotzsch and hereinafter referred to by the variety name 'NPCW10184'. The new variety is the result of a 30 gray radiation induced mutation in the parent plant 'Christmas Angel' (U.S. Plant Pat. No. 19,020) in 2007. A single plant selection was subsequently chosen for further evaluation and asexual propagation.

'NPCW10184' was first propagated via vegetative cuttings and has been asexually reproduced by vegetative cuttings in Stuttgart, Germany for over six generations. 'NPCW10184' has been found to retain its distinctive characteristics through successive asexual propagations via vegetative cuttings.

'NPCW10184' has not been sold or made publicly available more than one year prior to the filing date of this application.

SUMMARY OF THE INVENTION

The following are the most outstanding and distinguishing characteristics of this new variety when grown under normal horticultural practices in Stuttgart, Germany.

1. Very upright habit; and
2. Intensive marble color pattern.

DESCRIPTION OF THE PHOTOGRAPH

This new poinsettia plant is illustrated by the accompanying photograph which shows overall plant habit including blooms, and foliage of the plant; the colors shown are as true as can be reasonably obtained by conventional photographic procedures. The photograph is of a whole plant about four-months-old and in full flower.

DESCRIPTION OF THE NEW VARIETY

The following detailed description sets forth the distinctive characteristics of 'NPCW10184'. The data which define these characteristics were collected from asexual reproductions carried out in Stuttgart, Germany. The plant history was taken on four month-old plants grown in 13 cm pots from August to December 2009 with a minimum pinch date of 32 weeks. The plants were grown in a greenhouse covered with glass. Color readings were taken under natural light in the greenhouse. Color references are primarily to The R.H.S. Colour Chart of The Royal Horticultural Society of London (R.H.S.) (5$^{th}$ edition 2007).

DETAILED BOTANICAL DESCRIPTION OF THE NEW PLANT

Classification:
- *Family*.—Euphorbiaceae.
- *Botanical*.—*E. pulcherrima* Willd. ex Klotzsch.
- *Common*.—Poinsettia.

Parentage: 'Christmas Angel' (U.S. Plant Pat. No. 19,020).

Growth:
- *Time to produce a rooted cutting*.—3 to 4 weeks.
- *Blooming habit*.—Intermittent; blooms from end of November to January.
- *Flowering response time*.—Approximately 55 days from beginning of short days until flowering.
- *Keeping quality*.—Very good.

Plant:

*Form*.—Triangular.

*Growth habit*.—Upright.

*Height*.—20.0 cm to 25.0 cm.

*Width*.—20.0 cm to 25.0 cm.

*Number of branches*.—5 to 6.

*Average number of inflorescences per plant*.—5 to 6.

Stems:

*Color*.—Lower part: RHS 135C. Upper part: RHS 142B.

*Length*.—About 20.0 cm.

*Internode length*.—1.0 cm to 3.0 cm.

*Diameter*.—0.5 cm to 1.0 cm.

Leaves:

*Quantity*.—6 to 10 per lateral branch.

*Arrangement*.—Alternate.

*Shape*.—Ovate to lanceolate.

*Apex*.—Acuminate.

*Base*.—Truncate.

*Margin*.—Serrate.

*Lobes*.—Very few. Lobation characteristics: Shallow.

*Texture* (*both surfaces*).—Smooth.

*Vein color* (*both surfaces*).—RHS 135D.

*Variegation*.—Absent.

*Size*.—Length: 6.0 cm to 12.0 cm. Width: 4.0 to 7.0 cm.

*Color*.—Mature foliage: Upper surface: RHS 136A. Lower surface: RHS 138B. Immature foliage: Upper surface: RHS 143B. Lower surface: RHS 143C.

*Leaf petiole*.—Length: 2.0 cm to 4.0 cm. Diameter: 0.2 cm to 0.3 cm. Color (both surfaces): RHS 143C.

Inflorescence:

*Lastingness of inflorescence on the plant*.—3 to 4 weeks.

*Diameter*.—10.0 cm to 16.0 cm.

*Height*.—2.0 to 3.0 cm.

Bracts:

*Number of bracts per inflorescence*.—8 (with 4 to 6 secondary bracts).

*Shape*.—Ovate to lanceolate.

*Apex*.—Acuminate.

*Base*.—Rounded.

*Margin*.—Few shallow lobes.

*Size*.—Length: 6.0 cm to 10.0 cm. Width: 3.0 cm to 5.0 cm.

*Texture* (*both surfaces*).—Smooth.

*Vein color*.—Upper surface: RHS 1C. Lower surface: RHS 149D.

*Bract color*.—Upper surface: RHS 1C, center is between RHS 51B and RHS 51C. Lower surface: RHS 1C, center is RHS 51A and RHS 51B.

*Bract petiole*.—Length: 1.0 cm to 2.0 cm. Diameter: 0.2 cm. Color: Upper surface: RHS 47B. Lower surface: RHS 135D, moving to reddish.

Cyme:

*Diameter*.—2.0 cm to 3.0 cm.

*Cyathia number*.—8 to 15 per inflorescence.

*Cyathium*.—Shape: Ovate. Diameter: 0.3 cm to 0.5 cm. Length: 0.4 cm to 0.7 cm. Color: RHS 135C and RHS 142B.

*Peduncle*.—Color: RHS 142B. Length: 0.1 cm to 0.2 cm.

*Nectar cups*.—Number: 1 per cyathia. Diameter: 0.1 cm when closed, 0.2 cm when open. Size: 0.3 to 0.5 cm. Color: RHS 142C when closed, RHS 13B when open.

Reproductive organs:

*Stamens*.—Quantity: 10 to 15 per cyathia. Shape: Ovate.

*Filament*.—Length: 0.3 cm. Color: RHS 1D.

*Pollen*.—Quantity: Moderate. Color: RHS 9A.

*Gynoecium*.—Present.

Fruit and seed set: No fruit or seed have been observed.

Disease and insect/pest resistance: Good.

COMPARISON WITH COMMERCIAL VARIETY

'NPCW10184' differs from the commercial variety 'Christmas Angel' (U.S. Plant Pat. No. 19,020) by having marbled bracts that range in color from RHS 1C to between RHS 51B and RHS 51C, more cyathia per inflorescence, and more stamens per cyathia, while 'Christmas Angel' has red bracts (RHS 46B), fewer cyanthia per inflorescence, and fewer stamens per cyathia.

'NPCW10184' differs from the commercial variety 'Marblestar' (U.S. Plant Pat. No. 9,685) by having a pink color of RHS 47D and dark green leaves, while 'Marblestar' has a pink color of RHS 51B and 51C and light green leaves.

We claim:

1. A new and distinct variety of poinsettia plant named 'NPCW10184' as described and shown herein.

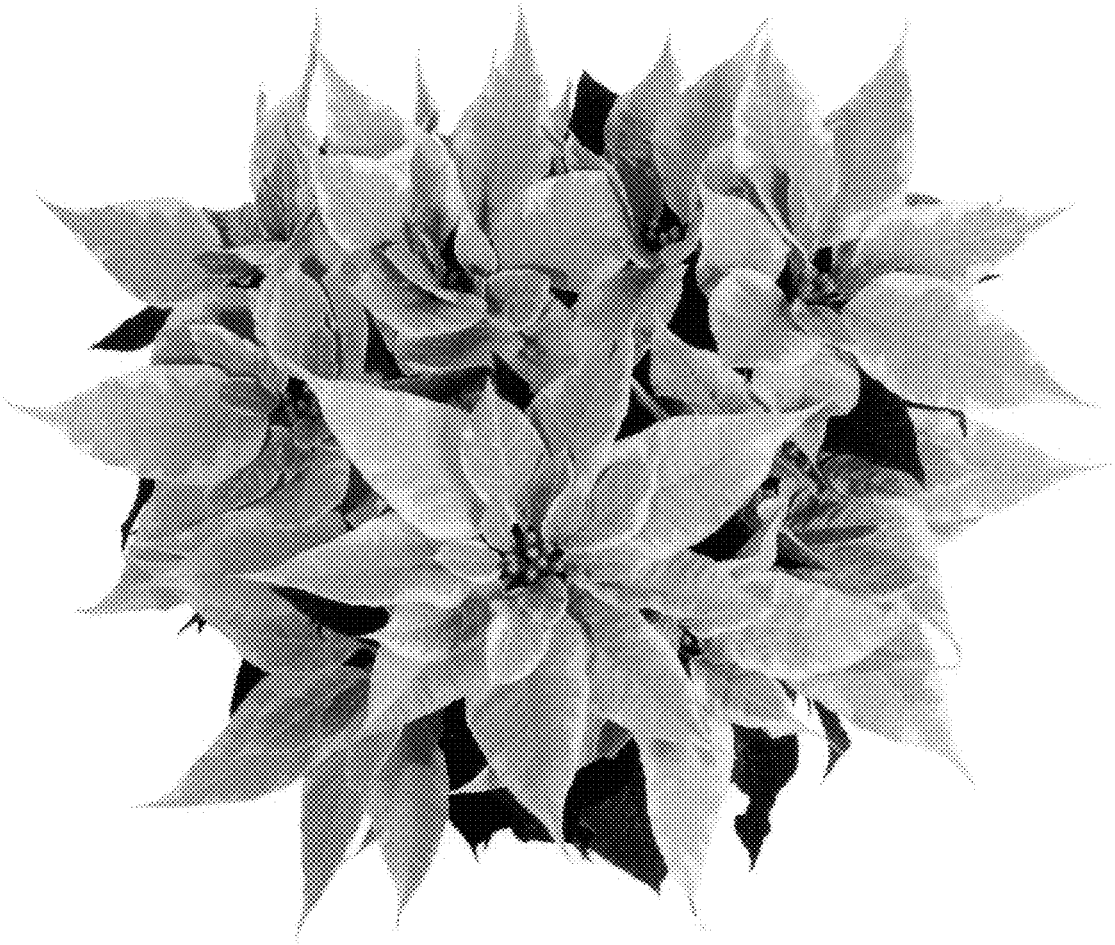

* * * * *